United States Patent
Wang et al.

(10) Patent No.: US 8,613,880 B2
(45) Date of Patent: Dec. 24, 2013

(54) POST ELECTRON BEAM CONDITIONING OF POLYMERIC MEDICAL DEVICES

(75) Inventors: Yunbing Wang, Sunnyvale, CA (US); Xiao Ma, San Jose, CA (US); Fuh-Wei Tang, Temecula, CA (US); Ni Ding, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 107 days.

(21) Appl. No.: 13/093,755

(22) Filed: Apr. 25, 2011

(65) Prior Publication Data

US 2011/0260358 A1    Oct. 27, 2011

Related U.S. Application Data

(63) Continuation-in-part of application No. 12/860,681, filed on Aug. 20, 2010, and a continuation-in-part of application No. 12/764,803, filed on Apr. 21, 2010.

(51) Int. Cl.
*B29B 17/00* (2006.01)
(52) U.S. Cl.
USPC ......................................................... 264/345
(58) Field of Classification Search
USPC ......................................................... 264/345
See application file for complete search history.

(56) References Cited

U.S. PATENT DOCUMENTS

| 5,650,485 | A | 7/1997 | Sun et al. |
| 7,297,758 | B2 | 11/2007 | Gale et al. |
| 2007/0032634 | A1 | 2/2007 | Gale et al. |
| 2007/0065334 | A1 | 3/2007 | Shalaby |
| 2007/0253996 | A1 | 11/2007 | Bin et al. |
| 2008/0169582 | A1 | 7/2008 | Dave et al. |
| 2011/0001271 | A1 | 1/2011 | Hossainy et al. |
| 2012/0045362 | A1 * | 2/2012 | Kleiner et al. ............... 422/22 |

FOREIGN PATENT DOCUMENTS

| EP | 0 218 003 | 4/1987 |
| EP | 1 872 808 | 1/2008 |
| JP | 11 133196 | 5/1999 |
| JP | 2000 334028 | 12/2000 |
| WO | WO 03/037390 | 5/2003 |
| WO | WO 2006/034157 | 3/2006 |
| WO | WO 2007/142736 | 12/2007 |
| WO | WO 2010/017090 | 2/2010 |
| WO | WO 2010/019448 | 2/2010 |

OTHER PUBLICATIONS

International Search Report for PCT/US2011/047974 mailed May 3, 2012, 10 pgs.
Milicevic et al., "Thermal and crystallization behaviour of gamma irradiated PLLA", Radiation Physics and Chemistry 76, pp. 1376-1380 (2007).
International Search Report for PCT/US2011/057932 mailed Apr. 5, 2012, 11 pgs.

* cited by examiner

*Primary Examiner* — Larry Thrower
(74) *Attorney, Agent, or Firm* — Squire Sanders (US) LLP

(57) ABSTRACT

Methods are disclosed for conditioning a polymeric stent after sterilization, and/or after crimping and before packaging, such that the properties of the polymeric stent fall within a narrower range of values. The stent is exposed to a controlled temperature at or above ambient for a period of time after radiation sterilization and/or after crimping and before sterilization. As a result, the polymeric stent properties, particularly radial strength and number-average molecular weight of the polymer of the polymeric stent, fall within a narrower range.

10 Claims, 7 Drawing Sheets

POST ELECTRON BEAM CONDITIONING OF POLYMERIC MEDICAL DEVICES

CROSS-REFERENCE TO RELATED APPLICATIONS

This application is a continuation-in-part of co-pending U.S. application Ser. No. 12/860,681, filed on 20 Aug. 2010, and is also a continuation-in-part of co-pending U.S. application Ser. No. 12/764,803, filed on 21 Apr. 2010. Both of these applications are incorporated by reference in their entirety, including any drawings, herein.

BACKGROUND OF THE INVENTION

1. Field of the Invention

This invention relates to methods making stents from bioabsorbable polymers.

2. Description of the State of the Art

This invention relates to radially expandable endoprostheses that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of scaffolding that includes a pattern or network of interconnecting structural elements or struts, that may be formed from wires, tubes, or sheets of material rolled into a cylindrical shape. This scaffolding gets its name because it physically holds open and, if desired, expands the wall of the passageway, or lumen. Typically, stents are capable of being compressed, or crimped, onto a catheter so that they can be delivered to and deployed at a treatment site. Delivery includes inserting the stent through small lumens, such as blood vessels, using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, the treatment of it can be challenging, as clinical options are more limited than for those lesions that were treated solely with a balloon.

Stents are used not only for mechanical intervention but also as vehicles for providing biological therapy. Biological therapy uses medicated stents to locally administer a drug. A medicated stent may be fabricated by coating the surface of either a metallic or polymeric scaffolding with a polymeric carrier that includes a drug. Polymeric scaffolding may also serve as a carrier of a drug.

It may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

One of the challenges of making medical devices out of polymers is that the properties of a polymer can change both during processing and after processing. These properties include mechanical properties such as strength and toughness as well as bioresorption kinetics. The processing steps in a fabrication process of a stent may be designed to maintain or instill in the stent particular ranges of the strength, toughness, and bioresorption, that are crucial for treatment with the stent. In some cases, properties of the polymer can change during additional processing operations and/or as a function of time during storage. Therefore, methods are needed that reduce, or eliminate undesirable changes in properties, and/or ameliorate their impact.

SUMMARY OF THE INVENTION

Various embodiments of the present invention include a method for conditioning a polymeric stent. The method may include the operations of: exposing a polymeric stent with a polymeric scaffolding to a temperature equal to, approximately equal to, or greater than 30° C. and not more than about 15° C. less than the glass transition temperature of the polymeric scaffolding for a duration of time. The duration of time may be at least 8 hours. The polymeric stent may have been crimped onto a delivery device, packaged, and sterilized prior to the exposure. The polymeric scaffolding may be formed from a polymeric article that has been deformed by the application of stress at a temperature greater than that of the glass transition temperature of the polymeric article, and the polymeric article may have a glass transition temperature greater than 25° C. The exposure temperature may be controlled to within ±3° C.

In an aspect of the invention, the polymeric article may be a polymer tube and the deformation under stress may comprise radial expansion of the polymer tube.

In another aspect of the invention, the polymeric scaffolding may include a polymer selected from the group consisting of poly(L-lactide), polymandelide, poly(DL-lactide), polyglycolide, poly(L-lactide-co-glycolide), and all combinations thereof in all proportions.

In another aspect of the invention, the exposure temperature may be not higher than 20° C. below the glass transition temperature of the polymeric scaffolding.

In another aspect of the invention, the duration of exposure may be from about 8 hours to about 20 days and the exposure temperature may be from about 32° C. to about 40° C.

In other aspects of the invention, the duration of exposure may be from about 1 day to about 10 days, or from about 2 days to about 6 days.

In another aspect of the invention, the exposure temperature may be in the range of about 35° C. to about 40° C.

In another aspect of the invention, the method may also include exposing the polymeric stent to a temperature equal to or greater than 35° C. and not more than about 10° C. greater than the glass transition temperature of the polymeric scaffolding for a duration of time where the duration of time may be in the range of from about 4 hours to about 10 days, and where the exposure may occur after the polymeric stent has been crimped onto a delivery device, but before the polymeric stent has been sterilized. The temperature of the exposure after crimping and before sterilization may be controlled to within ±3° C.

In another aspect of the invention, the duration of the exposure after crimping and before sterilizing may be from about 16 hours to about 48 hours, and the temperature of the exposure after crimping and before sterilization is from about 45° C. to about 65° C.

In another aspect of the invention, the duration of the exposure after crimping and before sterilizing may be from about 16 hours to about 32 hours, and the temperature of the exposure after crimping and before sterilization may be from about 50° C. to about 65° C.

In another aspect of the invention, the polymeric stent may be crimped onto a delivery device and the crimping may be performed at a temperature in the range of about 45° C. to about 50° C.

In another aspect of the invention, the polymeric stent may be crimped in the range of about 40° C. to about 55° C., and the post-sterilization exposure temperature may be about 33° C. and not more than about 37° C. and the duration of the exposure may be in the range of about 32 hours to about 84 hours.

In another aspect of the invention, the polymeric stent may be crimped onto a delivery device and the crimping may be performed at a temperature in the range of about 48° C., and the post-sterilization exposure temperature may be about 35° C. and the duration of the exposure may be in the range of about 48 hours to about 72 hours.

Various embodiments of the present invention include a method for conditioning a polymeric stent. The method includes the operations of: exposing a polymeric stent with a polymeric scaffolding consisting essentially of poly(L-lactide) to a temperature equal to, approximately equal to, or greater than 30° C. and not more than about 55° C. for a duration of time. The duration of time may be at least 8 hours. The polymeric stent may have been crimped onto a delivery device, packaged, and sterilized prior to the exposure. The polymeric scaffolding may be formed from a polymeric tube consisting essentially of poly(L-lactide) that has been deformed by the radial expansion of the polymeric tube at a temperature greater than that of the glass transition temperature of the polymeric tube. The exposure temperature may be controlled to within ±3° C.

In an aspect of the present invention, the duration of exposure after sterilization may be from about 8 hours to about 20 days and the exposure temperature may be from about 32° C. to about 40° C.

In an aspect of the present invention, the duration of exposure after sterilization may be from about 1 day to about 10 days.

In an aspect of the present invention, the duration of exposure after sterilization may be from about 2 days to about 6 days, and wherein the exposure temperature may be in the range of about 35° C. to about 40° C.

An aspect of the present invention, the method of exposing a poly(L-lactide) scaffolding also may include exposing the polymeric stent with the polymeric scaffolding to a temperature equal to or greater than 35° C. and not more than about 70° C. for a duration of time, where the duration of time may be from about 4 hours to about 6 days, after the polymeric stent has been crimped onto a delivery device, but before the polymeric stent has been sterilized. The temperature of the exposure after crimping and before sterilization may be controlled to within ±3° C.

In an aspect of the invention, for a polymeric stent with a poly(L-lactide) scaffolding, the duration of the exposure after crimping and before sterilizing may be from about 16 hours to about 48 hours, and the temperature of the exposure after crimping and before sterilization may be from about 45° C. to about 65° C.

In an aspect of the invention, for a polymeric stent with a poly(L-lactide) scaffolding, the duration of the exposure after crimping and before sterilizing may be from about 16 hours to about 32 hours, and the temperature of the exposure after crimping and before sterilization may be from about 50° C. to about 65° C.

In an aspect of the invention, for a polymeric stent with a poly(L-lactide) scaffolding, the polymeric stent may be crimped onto a delivery device at a temperature in the range of about 45° C. to about 50° C.

In an aspect of the invention, for a polymeric stent with a poly(L-lactide) scaffolding, the post-sterilization exposure temperature may be in the range from about 33° C. and not more than about 37° C., and the duration of the exposure may be in the range of about 32 hours to about 84 hours.

In an aspect of the invention, for a polymeric stent with a poly(L-lactide) scaffolding, the polymeric stent may be crimped onto a delivery device at a temperature of about 48° C., and the post-sterilization exposure temperature may be about 35° C., and the duration of the exposure after sterilization may be in the range of about 48 hours to about 72 hours.

Various embodiments of the present invention include a method for conditioning a polymeric stent. The method may include the operations of: exposing a polymeric stent with a polymeric scaffolding to a temperature equal to, approximately equal to, or greater than 30° C. and not more than about 55° C. for a duration of time until the radial strength is reduced by at least 10%. The duration of time may be at least 30 minutes, and the polymeric stent may have been crimped onto a delivery device, packaged, and sterilized prior to the exposure. The polymeric scaffolding may be formed from a polymeric tube that has been deformed by the radial expansion of the polymeric tube at a temperature greater than that of the glass transition temperature of the polymeric tube, and the exposure temperature may be controlled to within ±3° C. The glass transition temperature of the polymeric scaffolding may be greater than 25° C.

DETAILED DESCRIPTION OF THE INVENTION

Figure 1:
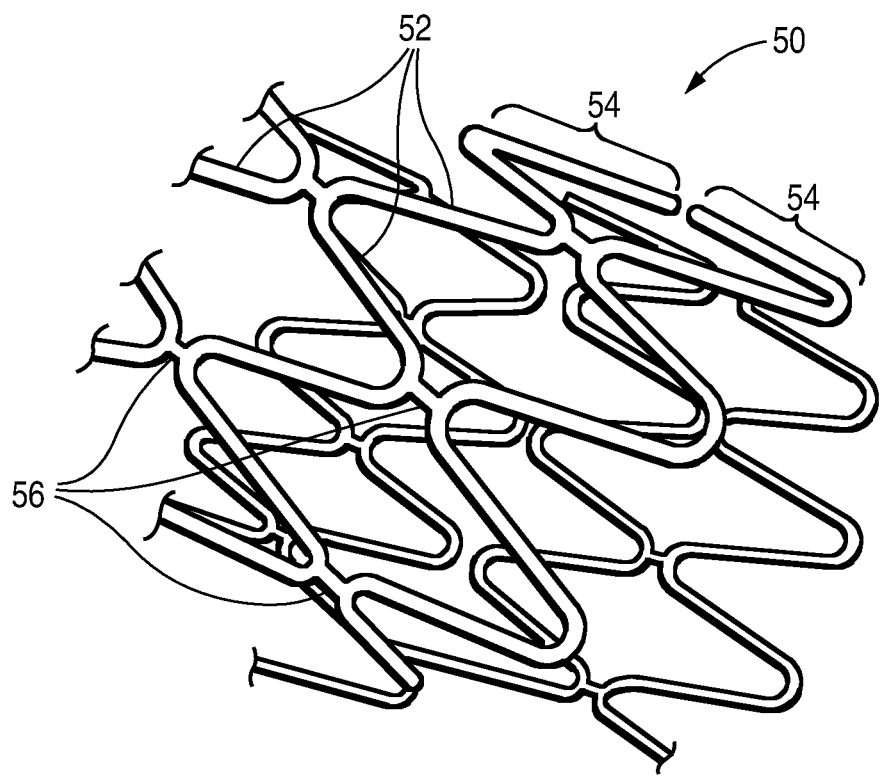
FIG. 1 depicts an exemplary stent.

Use of the term "herein" encompasses the specification, the abstract, and the claims of the present application.

Use of the singular herein includes the plural and vice versa unless expressly stated to be otherwise, or obvious from the context that such is not intended. That is, "a" and "the" refer to one or more of whatever the word modifies. For example, "a drug" includes one drug, two drugs, etc. Likewise, "the polymer" may refer to one, two or more polymers, and "the device" may mean one device or a plurality of devices. By the same token, words such as, without limitation, "polymers" and "devices" would refer to one polymer or device as well as to a plurality of polymers or devices unless, again, it is expressly stated or obvious from the context that such is not intended.

As used herein, unless specifically defined otherwise, any words of approximation such as without limitation, "about," "essentially," "substantially," and the like mean that the element so modified need not be exactly what is described but can vary from the description. The extent to which the description may vary will depend on how great a change can be instituted and have one of ordinary skill in the art recognize the modified version as still having the properties, characteristics and capabilities of the modified word or phrase. In general, but with the preceding discussion in mind, a numerical value herein that is modified by a word of approximation may vary from the stated value by ±15%, unless expressly stated otherwise.

Embodiments of the present invention relate to conditioning polymeric medical devices, such as stents, after radiation sterilization, such as electron beam (e-beam) sterilization, and after crimping the device onto a delivery device, but before sterilization. The conditioning improves the product such that the product properties are in a narrower range.

Although the discussion that follows focuses on a stent as an example of a medical device, the embodiments described herein are easily applicable to other medical devices, including implantable and insertable medical devices. More generally, embodiments of the present invention may also be applied to other devices, including, but not limited to, self-expandable stents, balloon-expandable stents, stent-grafts, vascular grafts, cerebrospinal fluid shunts, or generally tubular implantable medical devices including catheters.

Stents are typically composed of a pattern or network of circumferential and longitudinally extending interconnecting structural elements or struts. The pattern or network of struts form the scaffolding, or the device body, of a stent. In general, the pattern of the struts is designed to contact the lumen walls of a vessel and to maintain vascular patency. In general, a stent pattern is designed so that the stent can be radially compressed (crimped) and radially expanded (to allow deployment). Embodiments of the present invention are applicable to virtually any stent design and are, therefore, not limited to any particular stent design or pattern. One embodiment of a stent pattern may include cylindrical rings composed of struts. The cylindrical rings may be connected by connecting struts.

FIG. 1 depicts an example of a stent 50 comprising a plurality of interconnected stent struts 52 configured to move relative to each other. The stent struts 52 can be, for example, arranged in a sinusoidal or serpentine pattern. The stent struts 52 can form a plurality of circumferential rings 54 that may be arranged axially to form a tubular scaffold configured to support biological tissue after implantation of the stent. The rings may be connected by linking struts 56. There may be as few as one linking strut 56 per ring, but two, three, or more be present, or many more as depicted in FIG. 1. Although the cross-section of the struts in stent is shown as rectangular-shaped, the cross-section of the struts is not limited to those depicted, but may be circular, elliptical, or another cross-sectional shape.

All, substantially all, or some portion of the struts of the stent scaffolding can be made partially or completely from a biodegradable polymer, a biostable polymer, or a combination thereof. In such a case, a scaffolding composed of a polymer, or primarily of a polymer, provides the support or outward radial force to a vessel wall when implanted. As used herein, the terms biodegradable, bioabsorbable, bioresorbable, and bioerodable are used interchangeably and refer to materials such as polymers that are capable of being completely degraded and/or eroded when exposed to bodily fluids such as blood and can be gradually resorbed, absorbed, and/or eliminated by the body. The processes of breaking down and absorption of the material can be caused by, for example, hydrolysis and metabolic processes. Biostable refers to materials, such as polymers, that are not biodegradable.

As used herein, "polymeric stent" refers to a stent having a scaffolding that is made completely, or substantially completely, from a polymer, or the scaffolding is made from a composition including a polymer and another material. If the scaffolding is made from a composition including a polymer and another material, the polymer is a continuous phase of the scaffolding, the scaffolding is at least 50% by weight polymer, or the scaffolding is at least 50% by volume polymer. In some embodiments, a polymeric stent may have a scaffolding made from a composition including a polymer and another material that is at least 70%, at least 80%, at least 90%, or at least 95% by volume or by weight polymer. Analogous definitions apply to a polymeric tube, or a polymeric medical device except that the reference to the scaffolding would be replaced by "tube" for a polymer tube and "device body" for a medical device. The "device body" of a medical device is the functional device without a coating or layer of material different from that of which the device body is manufactured has been applied. If a device is a multi-layer structure, the device body is the layer(s) that form the functional device, and for a stent this would be the layer(s) which support the bodily lumen.

The scaffolding of the embodiments of the present invention can be made in entirely from, or in part from one or a combination of biodegradable polymers including, but not limited to, poly(L-lactide) (PLLA), polymandelide (PM), poly(DL-lactide) (PDLLA), polyglycolide (PGA), and poly (L-lactide-co-glycolide). The tube or stent scaffolding can also be made of any of the following: a random, alternating, or block copolymer of two or more of the above polymers; a random, alternating, or block copolymer of one or more of the above polymers, and one or more of the following: polycaprolactone (PCL), poly(trimethylene carbonate) (PTMC), polydioxanone (PDO), poly(4-hydroxy butyrate) (PHB), poly ethylene glycol (PEG), and poly(butylene succinate) (PBS); or any combination thereof. The PLGA used can include any molar ratio of L-lactide (LLA) to glycolide (GA). In particular, the stent can be made from PLGA with a molar ratio of (LA:GA) including 85:15 (or a range of 82:18 to 88:12), 95:5 (or a range of 93:7 to 97:3), or commercially available PLGA products identified as having these molar ratios. Combinations of polymers may be used and may be used in any proportions.

Polymers that may be used for struts of a bioabsorbable stent or other medical device include semicrystalline biodegradable polymers, such as biodegradable polyesters. In particular, the struts and/or scaffolding can be made substantially or completely out of biodegradable polyesters, or a composition including a biodegradable polyester, having a glass transition temperature (Tg) above body temperature, which is about 37° C. for a human (but embodiments of the present invention also encompass other animals). For example, this includes PLLA and PLGA. In some embodiments, the polymer is one having a glass transition temperature greater than 25° C., 30° C., 35° C., 40° C., 45° C., or 50° C. In some embodiments, the Tg is not more than 70° C., 75° C., or 80° C.

Table 1 below provides the Tg for some of the above polymers.

TABLE 1

Glass transition temperatures of polymers.

| Polymer | Glass-Transition Temperature (° C.)[1] |
| --- | --- |
| PGA | 35-40 |
| PLLA | 60-65 |
| PDLLA | 55-60 |
| 85/15 PLGA | 50-55 |
| 75/25 PLGA | 50-55 |
| 65/35 PLGA | 45-50 |
| 50/50 PLGA | 45-50 |

[1] Medical Plastics and Biomaterials Magazine, March 1998.

An exemplary embodiment is a PLLA scaffolding with a coating including PDLLA and everolimus. Another exemplary embodiment is a PLLA scaffolding with a coating including PDLLA and zotarolimus. Other exemplary embodiments encompass a scaffolding of PLGA with a molar ratio of (LA:GA) 85:15 (or a range of 82:18 to 88:12), or of PLGA with a molar ratio of (LA:GA) 95:5 (or a range of 93:7 to 97:3) with a coating including PDLLA and everolimus and/or zotarolimus.

A few of the more important design characteristics of stents are radial or hoop strength, expansion ratio, coverage area, and longitudinal flexibility. Fracture toughness is also an important characteristic as it minimizes or reduces cracking as the stent is crimped for delivery, and/or expanded during deployment. Selection of materials and use of specific processing steps ensure that the design characteristics of the stent are met.

In some embodiments, a stent may be formed from a polymeric or metallic tube by laser cutting the pattern of struts in the tube. Such tubes are typically formed by methods such as, but not limited to, extrusion or injection molding, as well as other conventional processes. The stent may also be formed by laser cutting a metallic or polymeric sheet, rolling the pattern into the shape of the cylindrical stent, and providing a longitudinal weld to form the stent. Other methods of forming stents are well known and include chemically etching a metallic or polymeric sheet and rolling and then welding it to form the stent.

In other embodiments, a metallic or polymeric filament or wire may also be coiled to form the stent. Filaments of polymer may be extruded, melt spun, solution spun or, eletrospun. These filaments can then be cut, formed into ring elements, welded closed, corrugated to form crowns, and then the crowns welded together by heat or solvent to form the stent. In other embodiments, the wires or filaments may be braided and/or interwoven to form the scaffolding of the stent.

The manufacturing process may further include radially expanding the tube to an expanded diameter and cutting a stent pattern in the expanded tube. The tube is radially expanded to increase its radial strength, which can also increase the radial strength of the stent subsequently formed from the expanded tube. The radial expansion process tends to preferentially align the polymer chains along the radial or hoop direction which results in enhanced radial strength. The radial expansion step is crucial to making a stent scaffolding with thin struts that is sufficiently strong to support a lumen upon implantation. In preferred embodiments, the PLLA scaffolding is formed from an extruded polymer tube, which prior to expansion, the tube may be completely amorphous or have a relatively low crystallinity, for example, less than 20%, less than 10%, or less than 5%.

The tube may be radially expanded by heating the tube to a temperature between Tg and the melting point of the polymer. At temperatures above Tg, the amorphous domains of a substance, such as a polymer, change from a brittle vitreous state to a solid deformable or ductile state. Upon expansion the tube is cooled to below the Tg of the polymer, typically to ambient temperature, where the tube is essentially maintained at an expanded diameter due to the fact that below Tg the polymer changes to a brittle vitreous state. In other words, the Tg corresponds to the temperature where the onset of segmental motion in the chains of the polymer occurs. For example, for a PLLA tube, an expansion temperature of 65-120° C. is preferred to optimize crystallinity and crystal size.

In addition to radial expansion, the tube can also be axially elongated or extended, before, during, and/or after, but preferably during, the radial expansion process. The percent radial expansion is defined as RE %=(RE ratio −1)×100%, where the RE Ratio=(Inside Diameter of Expanded Tube)/(Original Inside Diameter of the tube). The percent of axial extension that the polymer tube undergoes is defined as AE %=(AE ratio−1)×100%, where the AE Ratio=(Length of Extended Tube)/(Original Length of the Tube).

In preferred embodiments, the percent radial expansion may be between about 200% and 500%, preferably 400% to 500%, or any specific value within either of these ranges. The percent axial extension expansion may be between about 20% and about 200%, preferably about 20% and about 120%, or any specific value within either of these ranges. In preferred embodiments, the tube is a PLLA tube.

The tube may be optionally annealed after the radial and/or axial expansion. The annealing may be performed to relief residual stresses, and/or to stabilize the polymer. Increasing the temperature of the stent or tube above ambient may cause radial shrinkage (a decrease in diameter) or, in general, changes in shape such as warping along the axis of the stent or tube. This change in shape may be due to a release of residual stress that occurs during treatment. Thus, in further embodiments, radial shrinkage (strain recovery) or changes in shape can be reduced or prevented by restraining the stent or tube during treatment by, for example and without limitation, placing the tube or stent over a mandrel.

Polymers are viscoelastic materials that exhibit stress relaxation and strain recovery. When an ideal elastic material is subjected to a stress which is then released after a time period, the material recovers the original shape. A rubber band is a close approximation of this ideal perfectly elastic material. When an ideal viscous material is subjected to a stress which is then released after a time period, the material does not recover the original shape, but remains in the deformed shape. A liquid is an approximation of a purely viscous material. When a viscoelastic material is subjected to a stress which is released after a time period, the strain, that is the deformation, slowly recovers, but not completely to its' initial shape. The slow recovery results in a change in dimensions over time. Stress relaxation occurs when a viscoelastic material is held at a constant strain, or constant deformation, and the stress decreases, or "relaxes" over time as the polymer chains rearrange.

Annealing also may impact the fracture toughness which is enhanced for a semicrystalline polymer by minimizing the size of crystalline domains and achieving an optimal amorphous/crystalline ratio. The crystallinity provides strength and stiffness (high modulus) to the polymer which is needed for supporting a vessel. However, if the degree of crystallinity is too high, the polymer may be too brittle and is more susceptible to fracture. In some embodiments, the degree of crystallinity for a PLLA scaffolding may be about 10% to about 40%, or more narrowly, 30%-40%.

Figure 2:
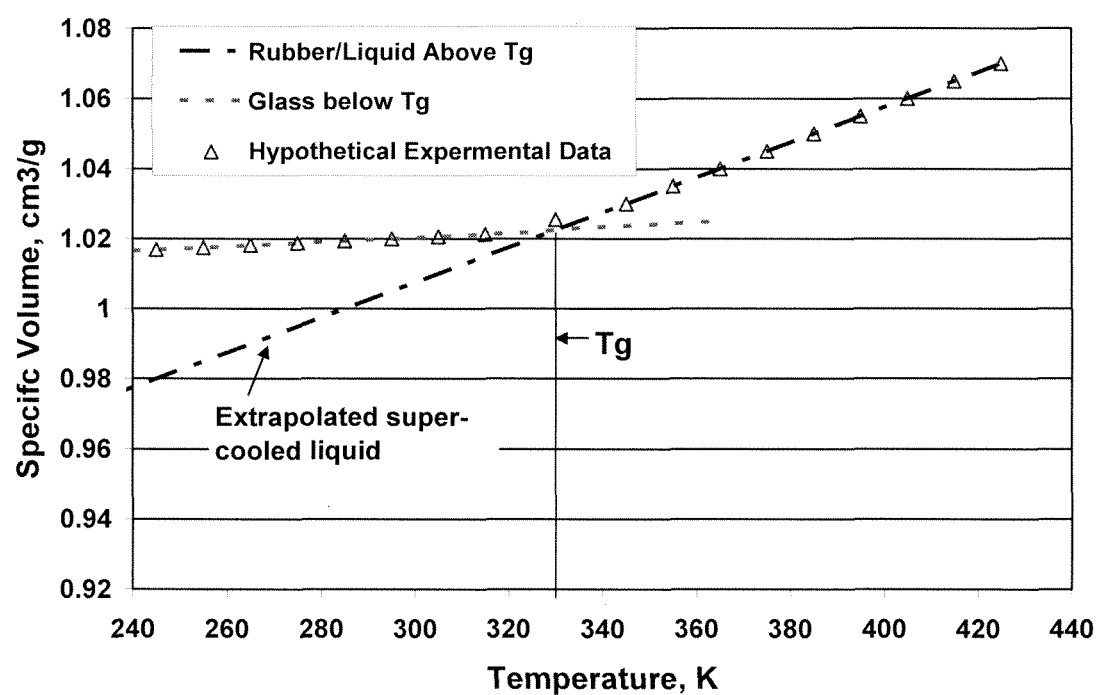
FIG. 2 depicts the specific volume of a polymer as a function of temperature.

Annealing may also help stabilize the polymer and/or ameliorate the effects of physical aging. Amorphous and semicrystalline polymers generally undergo physical aging during storage when the glass transition of the amorphous region is greater than the storage temperature. As shown in FIG. 2, a material that is amorphous or partially amorphous and is above it glass transition temperature will exhibit an inflection point or departure from a linear relationship between the specific volume and temperature as the polymer cools if cooling is at a non-equilibrium rate. At some point during cooling, the polymer chains do not have sufficient "time" to rearrange to the equilibrium state, and are thus trapped in a non-equilibrium state. After the inflection point which is the experimentally observed glass transition temperature marked as Tg in FIG. 2, the specific volume follows a different linear relationship with temperature. A polymer held ("aged") at a temperature below the glass transition temperature will densify over time if the rate of cooling was not an equilibrium rate. Cooling rates are almost always non-equilibrium rates in actual practice. This densification is illustrated by the arrow shown in FIG. 2. As the material densifies, the mechanical properties are also changing, generally becoming more brittle and less elastic. It is this gradual change in mechanical properties and densification which is referred to as the phenomenon of "physical aging."

After cutting a stent pattern into the expanded tube, the stent scaffolding may then be optionally coated with a coating which can include a polymer and another substance such as a radiopaque agent and/or a drug. In some embodiments, the coating is polymer free. Typically, a coating on a stent may be formed by applying or depositing a coating composition including the polymer and/or drug, and/or other materials, dissolved, and/or dispersed, in a solvent on the surface of the stent scaffolding. The coating composition can be applied to a stent scaffolding by various methods, such as, dip coating, brushing, or spraying. Spray coating a stent typically involves mounting or disposing a stent on a support, followed by spraying a coating composition from a nozzle onto the mounted stent in one or more passes with substantial solvent removal between passes which may involve application of heat.

In order to make the stent ready for delivery, the stent is secured to a delivery balloon. In this process, the stent is compressed to a reduced diameter or crimped over the balloon resulting in high stress and strain on the stent. Heating a stent during crimping can reduce or eliminate radially outward recoiling of a crimped stent which can result in an unacceptable profile for delivery. Crimping may also occur at an ambient temperature. Therefore, crimping may occur at a temperature ranging from 25° C. to 60° C., or higher, for a duration ranging from about 60 seconds to about 5 minutes.

Once the stent has been crimped onto a support element, such as and without limitation, a catheter balloon, the stent delivery device is packaged in sealed storage containers. Such containers are adapted to protect the assembly from damage and environmental exposure (humidity, oxygen, light, etc.) which can have an adverse effect on the stent. Storage containers for a stent and delivery system can be designed to be any convenient form or shape that permits the effective enclosure of a stent and delivery system assembly contained therein. A container intended primarily to protect the stent and delivery system from environmental exposure can be a pouch or sleeve. In preferred embodiments, the container is an aluminum based pouch and the pouch is filled with Argon or another inert gas. Thus, the crimped stent is packaged in an oxygen free environment.

After the stent is packaged, it is sterilized. Sterilization is typically performed on medical devices, such as stents and delivery systems, to reduce the bioburden. Bioburden refers generally to the number of microorganisms with which an object is contaminated. The degree of sterilization is typically measured by a sterility assurance level (SAL) which refers to the probability of a viable microorganism being present on a product unit after sterilization. The required SAL for a product is dependent on the intended use of the product. For example, a product to be used in the body's fluid path is considered a Class III device.

Radiation sterilization is well known to those of ordinary skill the art. Medical articles composed in whole or in part of polymers can be sterilized by various types of radiation, including, but not limited to, electron beam (e-beam), gamma ray, ultraviolet, infra-red, ion beam, x-ray, and laser sterilization. A sterilization dose can be determined by selecting a dose that provides a required SAL. A sample can be exposed to the required dose in one or multiple passes.

The stent may be sterilized by exposure to electron beam (e-beam) radiation, or some other type of radiation. The radiation exposure can be performed with a conventional e-beam radiation source. In some embodiments, the packaged stent may be exposed to a dose between 10-40, 20-35, or 20-30 kGy. In other embodiments, the stent may be exposed to a dose between 20-31 kGy or, more narrowly, 20-27.5 kGy.

Radiation exposure can degrade the properties of the polymers and drugs. In particular, the radiation can generate active species and induce chemical reactions in the polymer and drug. High-energy radiation such as e-beam and gamma radiation tends to produce ionization and excitation in polymer molecules. These energy-rich species undergo dissociation, subtraction, and addition reactions that degrade the properties of a polymer in a sequence leading to chemical stability. The stabilization process can occur during, immediately after, or even days, weeks, or months after irradiation which often results in physical and chemical cross-linking or chain scission. Chain scission can result in a reduction in molecular weight which can adversely affect mechanical properties, and, in the case of a degradable polymer, degradation properties. In contrast, cross-linking would tend to increase the molecular weight of the polymer. Resultant physical changes can include embrittlement, discoloration, odor generation, stiffening, and softening, among others.

Exposing a polymer to e-beam radiation causes the generation of free radicals in the polymer. The degradation of polymer properties has been associated with free radical generation caused by the radiation exposure. Free radicals generated can become trapped within the polymer. The change in the polymer properties may continue as the trapped free radicals continue to decay after the initial radiation exposure. "Free radicals" refer to atomic or molecular species with unpaired electrons on an otherwise open shell configuration. Free radicals can be formed by oxidation reactions. These unpaired electrons are usually highly reactive, so radicals are likely to take part in chemical reactions, including chain reactions. The free radicals formed due to radiation exposure can potentially react with the polymer chains to cause chain scission. These reactions are dependent on e-beam dose (more generally, radiation dose), dose rate, as well as the environment of irradiation (such as e-beam environment) including the type of gas present, the humidity, and the temperature.

The characteristics of the stents produced from the above process, that is extrusion of a polymer tube which is axially and radially expanded and optionally annealed, laser cut to form a stent pattern, coated with a drug delivery coating including a polymer and a drug, crimped onto a delivery device, packaged in an inert gas, such as argon, and sterilized by e-beam sterilization showed a drop in number-average molecular weight of the polymer of the scaffolding after sterilization. After sterilization, the molecular weight of the PLLA of a PLLA scaffolding is lower than the molecular weight of the PLLA of the PLLA scaffolding prior to sterilization. Thus, the sterilization process reduces the molecular weight of the PLLA polymer.

In addition, the presence of free radicals in the sterilized PLLA has been monitored and the concentration of the free radicals is seen to decrease with time after e-beam exposure. The decrease in concentration is believed to be primarily due to the termination of the free radicals through reactions with the polymer chains which may result in chain scission. The concentration of free radicals does not decay to zero until about 2 months under inert gas packaging condition.

Moreover, the PLLA stents produced as discussed above exhibited large variations in the product properties from lot to lot. In particular, the final products exhibited a wide variation in the number-average molecular weight of the PLLA polymer of the polymeric scaffolding and the radial strength of the polymeric stent as tested.

Figure 5:
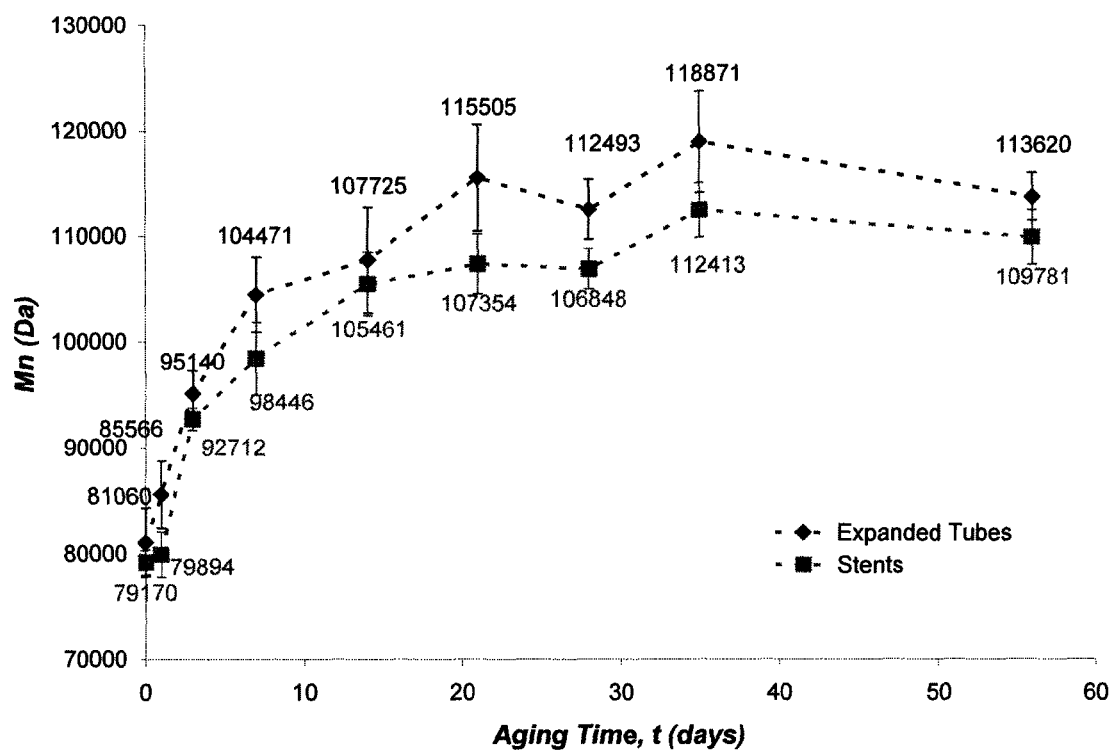
FIG. 5 depicts the number-average molecular weight of a polymer of a polymeric stent as a function of time after electron beam sterilization.

It was unexpectedly discovered that the polymeric stent continued to change after the final operation of e-beam sterilization. Thus, the properties of the polymeric stent scaffolding did not vary from one processing run to another, but it was the experimental testing protocol that varied. Specifically, due to the change in the properties with time, a variation in the time from manufacture to evaluation resulted in products apparently exhibiting a large variation in product properties. With respect to the number average molecular weight of the PLLA polymer, after the initial decrease in the molecular weight of a PLLA stent that has been sterilized with e-beam radiation, it was unexpectedly found that the molecular weight subsequently increases for a time period after sterilization. FIG. 5 provides an example of the number average molecular weight of a PLLA polymer in a PLLA stent and a PLLA tube as a function of time after sterilization by e-beam. The number average molecular weight of the polymer immediately after the e-beam sterilization is lower than that of the polymer prior to e-beam sterilization.

Figure 6:
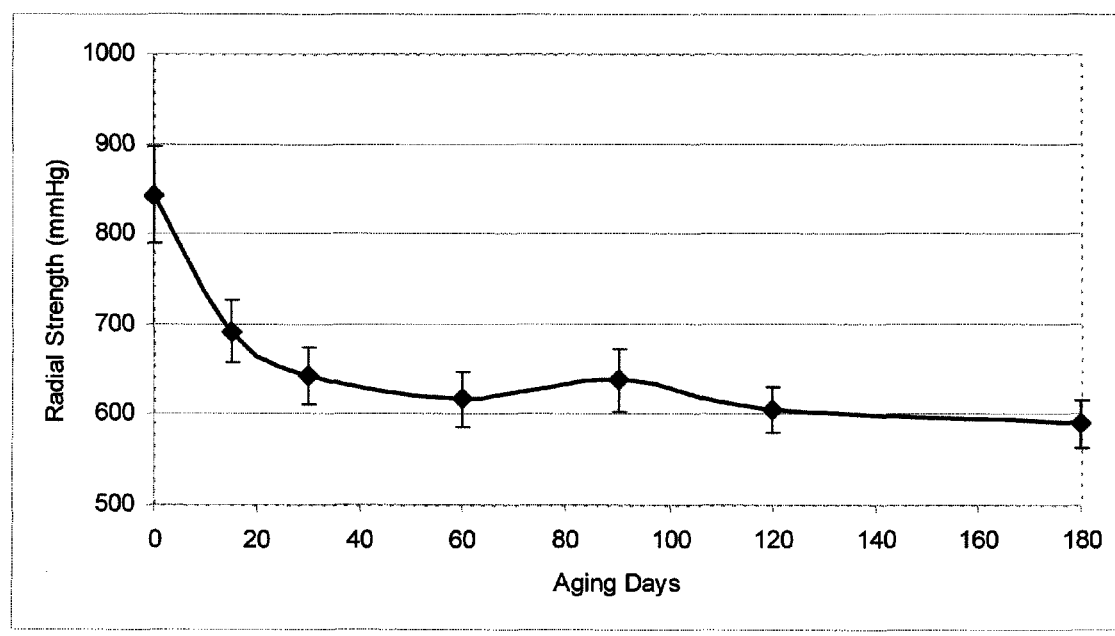
FIG. 6 depicts the radial strength of a polymeric stent as a function of time after electron beam sterilization.

Unexpectedly, in addition to changes in the number average molecular weight, it was observed that the radial strength decreases with time after sterilization. FIG. 6 illustrates the radial strength with time after sterilization by e-beam.

Therefore, methods are needed to improve the product by providing a method which results in a narrower range in the product properties, and particularly a narrower range at product release. The various embodiments of the present invention include methods of "conditioning" a packaged and sterilized stent, and or a crimped stent to obtain such improvement.

"Conditioning" a product may be exposing the product to an environment having a controlled temperature of about 28° C. or a specific controlled temperature above 28° C. for at least 0.5 hours. The exposure results in the product, and as a result the materials of which the product is formed, being heated to the exposure temperature, and subsequently being maintained at the exposure temperature for a duration of time. The duration of time of the exposure is greater than the duration of time during which the product is maintained at the specified controlled temperature because it takes some time to heat the product to the exposure temperature. The exposure may occur after sterilization and/or after crimping. "Conditioning" may be heating a product to a temperature at or above 28° C. in a controlled environment, and subsequently maintaining the product at that temperature in the controlled environment for at least 0.5 hours. The controlled environment may be one in which the temperature is controlled to within a specified range, or one in which temperature, pressure and/or some other variable are controlled within a specified range. "Conditioning" may be exposing a product to an environment of controlled temperature at or above 28° C., and potentially the environment is also at a controlled pressure, and/or other characteristics are controlled in the environment, such as % oxygen and/or humidity, for a duration of time sufficient to reach a specified value of a property. The specified value may be a "stabilized" value of the property, that is a pseudo steady-state value, or it may be a partially stabilized value. In some embodiments, the specified value is determined with reference to the pseudo-steady state or plateau value of the property. As a non-limiting example, as shown in FIG. 6, the radial strength changes from the initial time to about 60 days where it reaches a pseudo-steady state or plateau value. The specified value may be some specific percentage of the total change from the initial value to the plateau value. For example, the specified value may be a value which represents at least 25%, at least 30%, or at least 50% of the change from the initial to the plateau value. As an exemplary and not-limiting example, if the initial radial strength is 850 mmHg and the plateau value is 600 mmHG, then the total decrease is 250 mmHG, and therefore, a value of 800 mmHg radial strength would represent a radial strength decrease from the initial that is 20% of the total decrease (850-0.2*250)). For a polymeric stent, the initial value may be the value right before crimping, after crimping but before sterilization, or after sterilization. The specified value may also be a percent increase or decrease from the initial value without reference to the plateau value.

Without being bound by theory, it is believed that the exposure to increased temperature chemically stabilizes the polymer of the stent and accelerates the loss of free radicals. As discussed and shown below, exposing a PLLA stent to a temperature above ambient dramatically accelerates the reduction in concentration of the free radicals after radiation exposure. Also, without being bound by theory, it is believed that the increased stent temperature resulting from the exposure increases the rate of stress relaxation. The choice of an intermediate temperature and time regimen for the conditioning results in an optimum value of partial stabilization of both properties, and helps to improve the product because the properties of the polymeric stent fall within a narrower range after conditioning.

As discussed above, below Tg, polymer chains have very low mobility. Without being limited by theory, it is believed that when free radicals that are generated in a polymer that is well below its Tg, the free radicals are trapped by polymer chains that have very low mobility, for example, those chains near or at the amorphous—crystalline interface. However, it is believed that free radicals can be trapped even in completely amorphous polymers with no crystallinity. The trapping of free radicals is typical for a polymer such as PLLA with a Tg above body temperature that is sterilized at or near ambient temperature. Since the free radicals generated have very low mobility, the probability of free radicals combining and terminating is relatively low due to their low mobility. As the temperature of the polymer increases closer to or above Tg, polymer chain mobility increases. The mobility of free radicals increases which increases the probability of self-terminating reactions.

Without being bound by theory, it is believed that the change in the radial strength observed after sterilization by radiation results from stress relaxation. When the polymeric stent is crimped onto a delivery device, it is subjected to stress. As the stent is maintained in the crimped state, the polymer chains slowly rearrange over time, and thus, after some time, the polymer chains are not in the same configuration as immediately before the crimping operation. Without being bound by theory, there may be some partial loss of chain orientation and resultant decrease in radial strength due to the chain rearrangement. As discussed above, the mobility of the polymer chains increases as the temperature of the polymer approaches and surpasses the Tg. Thus, the rate at which the stress relaxes is a function of the temperature.

On the other hand, exposing the polymer to a temperature above Tg and below the melting temperature (Tm) or heating the polymer to a temperature above Tg and below Tm may result in changes in the crystallinity, crystal size, and alignment of polymer chains. Therefore, exposure or heating above Tg may also result in undesirable changes in microstructure. Such changes may include an increase in crystal size and degree of crystallinity and loss of radial alignment. Similarly, exposing the polymer to a temperature "close" to Tg or heating the polymer to a temperature "close" to Tg, particularly for a sustained period of time, may allow changes in the polymer, and in particular, loss of the chain orientation as the chains re-arrange to a more random, and thus more entropically favorable, configuration. Thus, the conditioning, that is the exposure to increased temperature with subsequent stent heating, should be performed at a temperature and for a duration that inhibits loss, or inhibits significant loss, of mechanical properties generated by the radial and/or axial expansion and in later pressing steps.

In some embodiments, the stent is conditioned after radiation sterilization, such as but not limited to e-beam sterilization, by being heated as a result of exposure to an environment at a specified temperature above ambient temperature, such as at or above 28° C., and left in the environment for a duration of time not less than 0.5 hour. For example, the stent can be exposed in a temperature controlled oven in which the temperature can be precisely controlled at a specified temperature or within a temperature range.

Thus, in some embodiments, the exposure temperature, and thus the temperature to which the stent is heated and maintained, can be a temperature that about 28° C., or in the range of 28° C. to about 15° C. below the Tg of the polymeric scaffolding of the stent. In preferred embodiments, the specific temperature of exposure is not more than about 20° C. below the Tg of the polymeric scaffolding of the stent. In some embodiments, the specific temperature of exposure is not more than about is about 25° C. below the Tg of the polymeric scaffolding of the stent.

Figure 7:
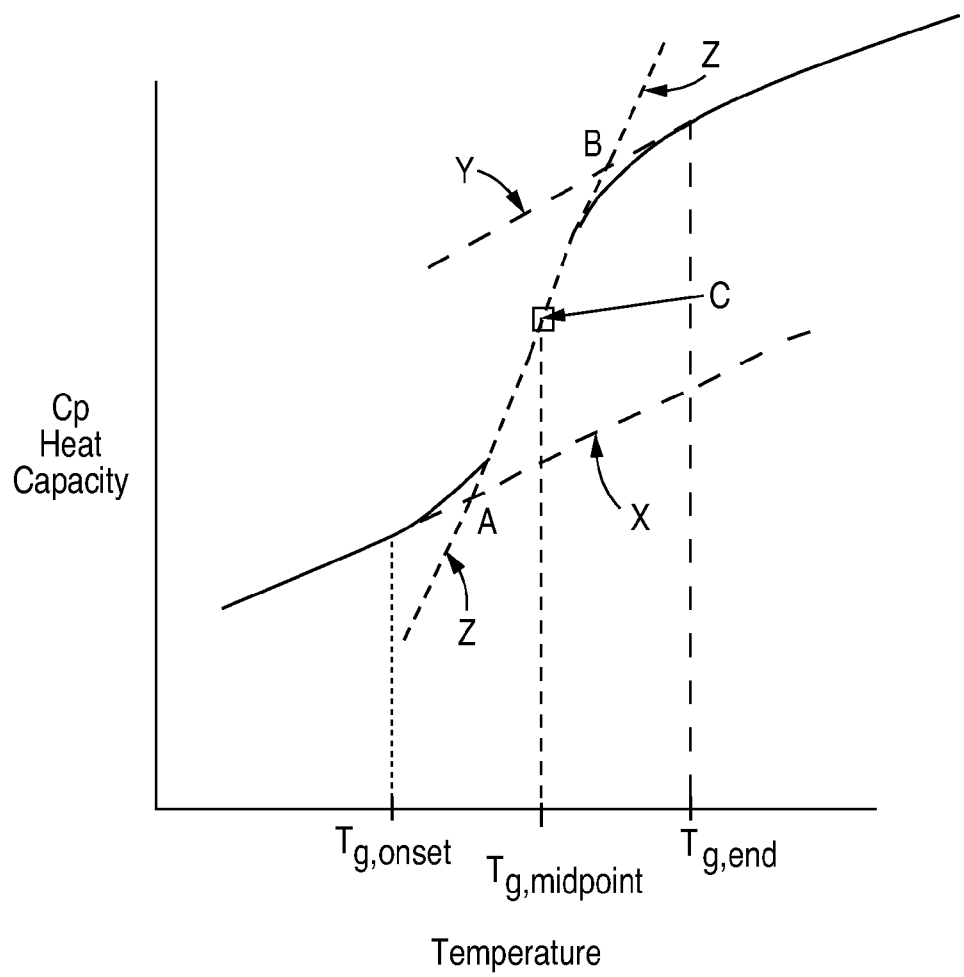
FIG. 7 depicts the heat capacity of a polymer as a function of temperature.

As used herein, the Tg of the polymeric scaffolding of the stent refers to the Tg of the scaffolding of the polymeric stent as measured by standard differential scanning calorimetry (modulated or unmodulated) with a temperature ramp of 5-40° C./min and if modulated, with a temperature modulation of 0.01 to 10° C. with a modulation period of 1 to 100 seconds, utilizing nitrogen or argon at a flow rate of 20-200 ml/min, or as determined as the mid-point in the change of the heat capacity in a plot of heat capacity versus temperature as illustrated in FIG. 7. FIG. 7 the heat capacity obtained via DSC versus temperature in the region of the glass transition. As shown in FIG. 7, the heat capacity at low temperatures below the glass transition is linear and as the temperature increases there is a large increase in the slope with another linear region followed by a decrease in slope at higher temperature. The temperature range of change from where slope changes at low temperature, through the intermediate region to the change in slope at higher temperatures is the glass transition region. The glass transition temperature can be determined by extrapolating a line fit from the linear region at low temperature (line X), extrapolating a line fit from the linear region at high temperature (line Z), and a line fitted along the steep linear region (line Z) extrapolated to higher and lower temperatures so that line Z intersects line X at A and line Y at B. The temperature at A is called Tg,onset and the temperature at B is Tg,end. The midpoint of Tg,onset and Tg along line Z (point C) is Tg,midpoint which is calculated from Tg,onset+½ (Tg,onset+Tg,end). Some sources defined the Tg as Tg,onset while other sources define Tg as Tg,midpoint. Unless otherwise specified, Tg refers to Tg,midpoint in the present application. Heat capacity determinations are typically more accurate when modulated DSC is used. The Tg that is measured is that of polymeric scaffolding in the "as processed condition," which includes any other additives in the scaffolding, but does not include any coating on the scaffolding. In other words, the Tg of the polymeric scaffolding may not be equivalent to the Tg of the polymer used in the fabrication of the scaffolding in the "as received" condition.

The polymeric scaffolding may be made from a blend of polymers, or a copolymer, either a random or block copolymer. In some polymer blends and copolymers, and particularly for block copolymers, two or more glass transition temperatures (Tgs) are observed. In general, the above temperature limits apply to the Tg that is above body temperature (about 37° C. for a human being, but the embodiments of the present invention are not limited to human beings as patients) if only one is above body temperature. In some embodiments, two or more Tgs may be above body temperature, and in such embodiments the specific temperature may be not more than about 15° C. below the lowest Tg. In general, the specific temperature may be not more than about 15° C. below the Tg of the polymer which contributes most significantly to the radial strength and toughness of the stent, but if two or more polymers have approximately equal contributions, the specific temperature is determined with reference to the lowest Tg of these two polymers. One of skill in the art is able to determine the relevant Tg(s) of the polymeric scaffolding based upon the disclosure herein.

The conditioning methods disclosed herein differ from merely placing a sterilized and packaged polymeric stent into storage for some time period. The standard United States Pharmacopeia (USP) storage conditions allow for a broad range in temperature, such as from 15° C. to 30° C. Storage of a packaged stent under conditions that are not precisely controlled may result in product properties that fall within a narrow range. In other words, if the conditions are not controlled, the product properties may stabilize or change by different amounts resulting in a broader distribution of product properties at release. To improve the product by having product properties in a narrower range at product release, the conditioning of the product may be under controlled conditions. Thus, embodiments of the present invention include storage or exposure under conditions that are precisely controlled. In some embodiments, the specific temperature may be controlled to be within ±5° C., preferably within ±3° C., more preferably, ±2° C., and even more preferably ±1.5° C.

In some embodiments, the stent is conditioned at, that is exposed to, a specified temperature or temperature range for a duration of time, followed by reducing the temperature of exposure, for example, back to ambient temperature.

In some embodiments, the specified temperature for conditioning, that is the temperature to which the stent is exposed and/or the temperature to which the stent is heated and at which it is subsequently maintained, for an arbitrary polymer with a Tg above body temperature (up to 15° C. below the Tg of the polymer) can be, in degrees Celsius, in the range of 25-30, 30-35, 35-40, 40-45, 45-50, 50-55, 55-60, 60-65, 65-70, 70-75, 75-80, 80-85, 85-90, 90-95, 95-100, or greater than 100. The specified temperature for conditioning can be in ranges of 1 or 2 degrees Celsius increments from 25° C. to a temperature that is 15° C. below the Tg of the polymeric scaffolding. The temperature range may be 32° C.-40° C., 33° C.-37° C., or 35° C.-40° C. The temperatures above and disclosed elsewhere herein can also apply to the actual temperature of the stent.

The specified temperature for conditioning for PLLA in degrees Celsius, can be, between 25-30, 30-35, 35-40, 40-45, or 45-50. The specified temperature for conditioning PLLA in degrees Celsius can also be in the range of 28-30, 30-32, 32-34, 34-36, 36-38, or 38-40. The specified temperature for conditioning can be any temperature, in degrees Celsius, between 25-40.

The specified temperature for conditioning for 85/15 and 75/25 PLGA can be in a temperature range, in degrees Celsius, of 25-30, 30-35, or 35-40. The specified temperature for conditioning for 85/15 and 75/25 PLGA can also be in a temperature range, in degrees Celsius, of 30-32, 32-34, 34-36, 36-38, 38-40, 40-42, 42-44, 44-46, 46-48, or 48-50° C. The specified temperature for conditioning can be any temperature between 25-50° C.

Embodiments of the present invention also encompass combinations of the above ranges that result in a contiguous range. As a non-limiting example, the following temperature ranges in degrees Celsius, 32-34, 34-36, 36-38, and 38-40, can be combined to obtain the temperature range 32-40 also expressed in degrees Celsius.

The duration of the conditioning, that is it may be the duration of the exposure at the specified temperature or it may be the duration that the stent is maintained at the specified temperature after heating to the specified temperature, in combination with any of the disclosed temperature embodiments, can be 4 hours to 20 days, less than 4 hours, or greater than 20 days. The duration of exposure or the duration of stent heating, in combination with any of the disclosed temperature embodiments, can be 0.5 hours to 1 hour, 0.5 hours to 2 hours, 0.5 hours to 24 hours, 0.5 hours to 32 hours, 4 hours to 8 hours, 8 hours to 16 hours, 8 hours to 18 hours, 8 hours to 20 hours, 8 hours to 36 hours, 4 hours to 32 hours, 8 hours to 48 hours, 16 hours to 32 hours, 16 hours to 48 hours, 16 hours to 72 hours, 36 hours to 120 hours, 36 hours to 4 days, 0.5 days to 1 day, 0.5 day to 2 days, 0.5 day to 3 days, be 0.5 day to 4 days, 0.5 day to 5 days, 0.5 to 10 days, 0.5 to 12 days, 0.5 to 15 days, 0.5 to 20 days, 1 day to 2 days, 1 day to 3 days, 1 day to 4 days, 1 day to 5 days, 1 day to 6 days, 1 day to 8 days, 1 day to 10 days, 1 day to 12 days, 1 day to 15 days, 1 day to 20 days, 1 day to 21 days, 2 days to 3 days, 2 days to 4 days, 2 days to 5 days, 2 days to 6 days, 2 days to 7 days, 2 days to 8 days, 2 days to 9 days, 2 days to 10 days, 2 days to 12 days, 2 days to 15 days, 2 days to 20 days, 3 days to 4 days, 3 days to 5 days, 3 days to 6 days, 3 days to 7 days, 3 days to 8 days, 3 days to 9 days, 3 days to 10 days, 3 days to 12 days, 3 days to 15 days, 3 days to 20 days, 4 days to 5 days, 4 days to 6 days, 4 days to 8 days, 4 days to 10 days, 4 days to 12 days, 4 days to 15 days, 4 days to 16 days, 4 days to 20 days, 4 days to 5 days, 5 days to 6 days, 5 days to 7 days, 5 days to 8 days, 5 days to 10 days, 5 days to 15 days, 5 days to 18 days, 5 days to 20 days, 6 days to 8 days, 6 days to 10 days, 6 days to 12 days, 6 days to 15 days, 6 days to 18 days, 6 days to 20 days, 7 days to 8 days, 7 days to 9 days, 7 days to 10 days, 7 days to 12 days, 7 days to 14 days, 7 days to 18 days, 7 days to 20 days, 8 days to 9 days, 8 days to 10 days, 8 days to 12 days, 8 days to 14 days, 8 days to 15 days, 8 days to 16 days, 8 days to 18 days, 8 days to 20 days, 9 days to 10 days, 9 days to 11 days, 9 days to 15 days, 9 days to 16 days, 9 days to 18 days, 9 days to 20 days, 10 days to 11 days, 10 days to 12 days, 10 days to 14 days, 10 days to 15 days, 10 days to 20 days, 10 days to 11 days, 10 days to 12 days, 10 days to 14 days, 10 days to 15 days, 10 days to 16 days, 10 days to 18 days, 10 days to 20 days, 11 days to 12 days, 11 days to 15 days, 11 days to 20 days, 12 days to 13 days, 12 days to 14 days, 12 days to 15 days, 12 days to 16 days, 12 days to 18 days, 12 days to 20 days, 15 days to 16 days, 15 days to 18 days, 15 days to 20 days, 16 days to 18 days, 16 days to 20 days, or 18 days to 20 days. Embodiments of the present invention also encompass durations in which each of the above lower and upper limits is preceded by "about." For example, about 18 days to about 20 days.

In preferred embodiments, the polymeric scaffolding is completely, or essentially completely, made of PLLA, PLGA with a molar ratio of (LA:GA) 85:15 (or a range of 82:18 to 88:12), or PLGA with a molar ratio of (LA:GA) 95:5 (or a range of 93:7 to 97:3), the specific temperature of the conditioning is 30° C. to 35° C., controlled to within at least ±3° C. or at least ±2° C., and the conditioning duration is from 1 day to 12 days, preferably, from 3 days to 8 days, and more preferably, from 5 days to 7 days.

In other preferred embodiments, the polymeric scaffolding is completely, or essentially completely, made of PLLA, PLGA with a molar ratio of (LA:GA) 85:15 (or a range of 82:18 to 88:12), or PLGA with a molar ratio of (LA:GA) 95:5 (or a range of 93:7 to 97:3), the specific temperature of the conditioning is in the range of 28° C. to 32° C., such as without limitation, 30° C., and the specific temperature is controlled to within at least ±3° C. or at least ±2° C., with a duration of the conditioning is from 0.5 day to 20 days, preferably, from 1 day to 15 days, more preferably from 2 days to 10 days, and even more preferably from 3 days to 8 days.

In other preferred embodiments, the polymeric scaffolding is completely, or essentially completely, made of PLLA, PLGA with a molar ratio of (LA:GA) 85:15 (or a range of 82:18 to 88:12), or PLGA with a molar ratio of (LA:GA) 95:5 (or a range of 93:7 to 97:3), the specific temperature of the conditioning is in the range is in the range of 32° C. to 37° C., such as without limitation, 35° C., controlled to within at least ±3° C. or at least ±2° C., and for a duration of the conditioning that is from 0.5 day to 15 days, preferably, from 1 day to 10 days, more preferably from 1 day to 8 days, and even more preferably from 1 day to 6 days.

In other preferred embodiments, the polymeric scaffolding is completely, or essentially completely, made of PLLA, PLGA with a molar ratio of (LA:GA) 85:15 (or a range of 82:18 to 88:12), or PLGA with a molar ratio of (LA:GA) 95:5 (or a range of 93:7 to 97:3), the specific temperature of the conditioning is in the range of 30° C. to 36° C., such as without limitation, 33° C., controlled to within at least ±3° C. or at least ±2° C., and for a duration of the conditioning that is from 0.5 day to 15 days, preferably, from 1 day to 10 days, more preferably from 1 day to 8 days, and even preferably from 1 day to 6 days.

In further embodiments, the polymeric stent may be conditioned in two "conditioning" stages, one after crimping but prior to sterilization and one after the sterilization. The conditioning stage after crimping may be before or after packaging. For the conditioning stage after crimping, the specific temperature of the conditioning may be from about 32° C. to about 15° C. higher than the glass transition temperature of the polymer, and the duration of the exposure and/or heating and maintenance may be at least 0.5 hours.

In some embodiments of conditioning after crimping and before sterilizing, the specified temperature for conditioning for an arbitrary polymer with a Tg above body temperature (up to 15° C. above the Tg of the polymer) can be, in degrees Celsius, in the range of 33-35, 35-40, 40-45, 45-50, 50-55, 55-60, 60-65, 65-70, 70-75, 75-80, 80-85, 85-90, 90-95, 95-100, or greater than 100. The specified temperature for conditioning can be in ranges of 1 or 2 degrees Celsius increments from 35° C. to a temperature that is 15° C. above the Tg of the polymeric scaffolding. In a preferred embodiments, the temperature for the conditioning may be not more than 10° C. above the Tg of the polymeric scaffolding.

The specified temperature for conditioning for PLLA in degrees Celsius, can be, between 33-35, 35-40, 40-45, 45-50, 50 -55, 55-60, 60-65, 65-70, 70-75, or 75-80. The specified temperature for conditioning for PLLA in degrees Celsius can also be in the range of 32-34, 34-36, 36-38, 38-40, 39-40, 40-42, 42-44, 44-46, 46-48, 48-50, 50-52, 52-54, 54-56, 56-58, 58-60, 60-62, 62-64, 64-66, 66-68, 68-70, 70-72, 72-74, 74-76, 76-78 or, 78-80. The specified temperature for conditioning can be any temperature, in degrees Celsius, between 25-80.

In preferred embodiments of the conditioning stage after crimping but before sterilizing, the specific temperature for conditioning is in the range of 50° C. to 65° C., and the duration is from 1 hour to 32 hours, and may also include a conditioning stage after sterilizing where the specific temperature is in the range of 33° C. to 37° C., and the duration is from 16 hours to 80 hours, 20 hours to 76 hours, or 24 hours to 72 hours.

In preferred embodiments for the two stage conditioning, the polymeric scaffolding is completely, or essentially completely, made of PLLA, PLGA with a molar ratio of (LA:GA) 85:15 (or a range of 82:18 to 88:12), or PLGA with a molar ratio of (LA:GA) 95:5 (or a range of 93:7 to 97:3), and for the initial conditioning stage after crimping and before sterilizing the specific temperature of the conditioning is in the range of 50° C. to 65° C., such as without limitation, 55° C., controlled to within at least ±3° C. or at least ±2° C., and for a duration from 0.5 hour to 32 hours, preferably, from 1 hour to 28 hours, and more preferably from 1 hour to 24 hours. For the second conditioning stage after sterilizing, the specific temperature of the conditioning is in the range of 33° C. to 37° C., such as without limitation, 35° C., controlled to within at least ±3° C. or at least ±2° C., and for a duration from 0.5 day to 10 days, preferably, from 1 day to 8 days, more preferably from 1 day to 6 days, and even more preferably from 36 hours to 80 hours.

In any of the embodiments, the conditioning can be performed by cycling the exposure temperature, and, thus the actual temperature of the stent. The temperature cycling can be performed by increasing the exposure temperature, decreasing the exposure temperature, and then repeating the increasing and decreasing one or more times. In such embodiments, the exposure temperature may be increased to a peak temperature followed by a decrease to a minimum temperature. The peak temperature and minimum temperature can be the same every cycle or can be vary from cycle to cycle. The temperature may be held constant for a period of time at the peak and/or minimum temperature. The hold time periods may vary with each cycle, or may be constant for some or all cycles. In some embodiments, the duration of the exposure and/or heating may be determined by only including the time periods at the peak temperature. In alternative embodiments, the duration of the exposure and/or heating may be determined by including all of the time during the cycle. In still other embodiments, the duration of exposure may be determined as that portion of the cycle exceeding any specified temperature between the minimum and peak temperatures. In some embodiments, both the peak and the minimum temperature are within the range of equal to or about equal to 25° C. to 15° C. below the Tg of the polymeric scaffolding, and the duration is determined by including all time within the cycle. If the exposure is by temperature cycling, the temperature is controlled be within ±5° C., preferably within ±3° C., more preferably, ±2° C., and even more preferably ±1.5° C. of the set-point or the intended temperature profile.

In embodiments with two stages of conditioning, neither, either one, or both stages may include temperature cycling. If both stages include temperature cycling, the pattern and number of cycles may be the same in each stage or different.

The temperature cycling exposure to the stent can be performed, for example, by disposing the stent in a temperature-controlled oven. The oven can be programmed to expose the stent to a selected time versus temperature profile.

In any of the conditioning embodiments, the controlled environment may include controlling other variables aside from the temperature. The controlled environment may be one where the pressure is at one atmosphere. The controlled environment may be essentially humidity free (less than 5% relative humidity (rh), less than 1% rh, or less than 1000 ppm water, where ppm may be by mass or by volume), or it may be a low humidity environment such for example and without limitation, between 5% and 15% rh, between 5% and 20% rh, or between 10% and 30% rh. The controlled environment may be one which is free of oxygen, or essentially free of oxygen (less than 1000 ppm oxygen, or less than 100 ppm oxygen where ppm may be by volume or by mass).

In still other embodiments, the polymeric stent can be crimped onto a delivery device at a specified temperature from 43° C. to 53° C., such as in any of the following temperature ranges in degrees Celsius or combinations of these temperature ranges: 43-44, 44-45, 45-46, 46-47, 47-48, 48-49, 49-50, 50-51, 51-52, or 52-53. Other embodiments of the present invention encompass crimping at a temperature in the range of 44° C. to 52° C., 45° C. to 51° C., 46° C. to 50° C., and 47° C. to 49° C. In still other embodiments, crimping occurs at about 48° C. For any of the above crimping embodiments, the stent may also be conditioned after sterilizing according to any of the above embodiments for conditioning after sterilization.

In preferred embodiments, the crimping is performed in any of the above temperature ranges, and the polymeric stent is conditioned after sterilization where the specific temperature of the exposure and/or the specific temperature to which the stent is heated and subsequently maintained is in the range of 33° C. to 37° C., such as without limitation, 35° C., controlled to within at least ±3° C. or at least ±2° C., and for a duration from 0.5 day to 10 days, preferably, from 1 day to 8 days, more preferably from 1 day to 6 days, and even more preferably from 36 hours to 80 hours.

In some embodiments, crimping is performed in any of the above temperature ranges, and two stages of conditioning as recited in any of the above embodiments are preformed. However, in preferred embodiments, the polymeric stent is only conditioned after sterilizing, or the polymeric stent is conditioned after sterilizing is performed and either crimped in the specified temperature range or conditioned after crimping but before sterilizing is performed, but not both.

In some embodiments, as a result of the conditioning, whether one-stage or two-stage, with or without temperature cycling, and with or without crimping in a specified temperature range, the radial strength of the stent may be at least 10% lower than the initial radial strength, where the initial radial strength is that measured within about 8-12 hours after the completion of the e-beam sterilization for one stage conditioning, or within about 8-12 hours after the completion of the crimping operation for two stage conditioning. In other embodiments, the radial strength of the stent may be 10% to 20% lower than the initial radial strength, 20% to 30% lower than the initial radial strength, 30% to 40% lower than the initial radial strength, or 20% to 40% lower than the initial radial strength.

In some embodiments, the change in radial strength is determined as a percent of the total decrease from the initial radial strength to the plateau radial strength which is illustrated by the value after about 60 days in FIG. 6. In some embodiments, as a result of conditioning, the radial strength is at a value that represents about 20% to about 30% of the total decrease from the initial value to the plateau, a value that represents about 20% to about 40% of the total decrease from the initial value to the plateau, a value that represents about 30% to about 50% of the total decrease from the initial value to the plateau, or a value that represents about 40% to about 60% of the total decrease from the initial value to the plateau.

In some embodiments, as a result of the conditioning, whether one-stage or two-stage, with or without temperature cycling, and with or without crimping in a specified temperature range, the number-average molecular weight of the polymer of the polymeric scaffolding may be at least 10% greater than the initial number-average molecular weight, where the initial number-average molecular weight is that measured within about 8-12 hours after the completion of the e-beam sterilization for either one stage or two-stage conditioning. In other embodiments, the number-average molecular weight of the polymer of the polymeric scaffolding may be 10% to 20% greater than the initial number-average molecular weight, 20% to 30% greater than the initial number-average molecular weight, 20% to 40% greater than the initial number-average molecular weight, or 30% to 50% greater than the initial number-average molecular weight. For those embodiments in which the polymeric scaffolding includes a polymer blend, the number-average molecular weight referred to is that of the polymer that contributes most significantly to the radial strength and toughness of the stent, but, if two or more polymers have approximately equal contributions, the number-average molecular weight may be an average of the two or more (keeping in mind the correct methods of averaging polymer molecular weights). One of skill in the art is able to determine the relevant number-average molecular weight of the polymer of the polymeric scaffolding based upon the disclosure herein.

In some embodiments, the change in number-average molecular weight is measured as a percent of the total increase from the initial value to the pseudo-steady state or plateau value which is illustrated by the value after about 21 days in FIG. 5. In some embodiments, as a result of conditioning, the number-average molecular weight is at a value that represents about 20% to about 30% of the total increase from the initial value to the plateau, a value that represents about 20% to about 40% of the total increase from the initial value to the plateau, a value that represents about 30% to about 50% of the total increase from the initial value to the plateau, or a value that represents about 40% to about 60% of the total increase from the initial value to the plateau.

In still further embodiments, the conditioning, whether one-stage or two-stage, with or without temperature cycling, and optionally combined with crimping in a specified temperature range, may be performed at a specified temperature and for a duration such that the radial strength of the polymeric stent is reduced by not less than 10%, between 10% and 15%, between 10% and 15%, between 15% and 20%, between 20% and 25%, or more than 25%, such as 25% to 50%, compared to the initial radial strength.

In still further embodiments, the conditioning, whether one-stage or two-stage, with or without temperature cycling, and optionally combined with crimping in a specified temperature range, may be performed at a specified temperature and for a duration such that number-average molecular weight of the polymer of the polymeric scaffolding is increased by at least 10%, from about 10% to about 20%, from about 20% to about 30%, from about 30% to about 40%, or from about 40% to about 60% as compared to the initial number-average molecular weight.

In still further embodiments, the conditioning, whether one-stage or two-stage, with or without temperature cycling, and optionally combined with crimping in a specified temperature range, may be performed at a specified temperature and for a duration such that the radial strength of the polymeric stent is at a value that represents about 20% to about 30% of the total decrease from the initial value to the plateau, a value that represents about 20% to about 40% of the total decrease from the initial value to the plateau, a value that represents about 30% to about 50% of the total decrease from the initial value to the plateau, or a value that represents about 40% to about 60% of the total decrease from the initial value to the plateau.

In still further embodiments, the conditioning, whether one-stage or two-stage, with or without temperature cycling, and optionally combined with crimping in a specified temperature range, may be performed at a specified temperature and for a duration such that number-average molecular weight of the polymer of the polymeric scaffolding is at a value that represents about 20% to about 30% of the total increase from the initial value to the plateau, a value that represents about 20% to about 40% of the total increase from the initial value to the plateau, a value that represents about 30% to about 50% of the total increase from the initial value to the plateau, or a value that represents about 40% to about 60% of the total increase from the initial value to the plateau.

Definitions

Ambient temperature can correspond to any temperature between 20° C. and 25° C.

All ranges disclosed include endpoints of the ranges.

As used herein, a "polymer" refers to a molecule comprised of, actually or conceptually, repeating "constitutional units." The constitutional units derive from the reaction of monomers. As a non-limiting example, ethylene ($CH_2=CH_2$) is a monomer that can be polymerized to form polyethylene, $CH_3CH_2(CH_2CH_2)_nCH_2CH_3$ (where n is an integer), wherein the constitutional unit is —$CH_2CH_2$—, ethylene having lost the double bond as the result of the polymerization reaction. Although poly(ethylene) is formed by the polymerization of ethylene, it may be conceptually thought of being comprised of the —$CH_2$— repeating unit, and thus conceptually the polymer could be expressed by the formula $CH_3(CH_2)_mCH_3$ where m is an integer, which would be equal to 2n+2 for the equivalent number of ethylene units reacted to form the polymer. A polymer may be derived from the polymerization of two or more different monomers and therefore may comprise two or more different constitutional units. Such polymers are referred to as "copolymers." "Terpolymers" are a subset of "copolymers" in which there are three different constitutional units. The constitutional units themselves can be the product of the reactions of other compounds. Those skilled in the art, given a particular polymer, will readily recognize the constitutional units of that polymer and will equally readily recognize the structure of the monomer from which the constitutional units derive. Polymers may be straight or branched chain, star-like or dendritic, or one polymer may be attached (grafted) onto another. Polymers may have a random disposition of constitutional units along the chain, the constitutional units may be present as discrete blocks, or constitutional units may be so disposed as to form gradients of concentration along the polymer chain. Polymers may be cross-linked to form a network.

As used herein, a polymer has a chain length of 50 constitutional units or more, and those compounds with a chain length of fewer than 50 constitutional units are referred to as "oligomers." As used to differentiate between oligomers and polymers herein, the constitutional unit will be the smallest unique repeating unit. For example, for poly(lactide) the constitutional unit would be

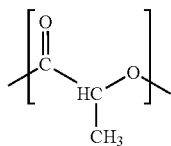

even though the polymer may be formed by the reaction of the cyclical dimer, lactide,

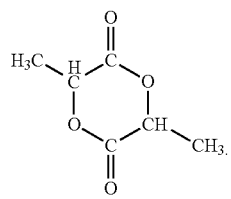

Similarly, for poly(ethylene) the constitutional unit used to count the "number" of constitutional units would be —$CH_2$— units, even though conventionally the constitutional unit is stated to be —$CH_2CH_2$— because it is always derived from the reaction of ethylene.

The "glass transition temperature," Tg, is the temperature at which the amorphous domains of a substance, typically a polymer, change from a brittle vitreous state to a solid deformable or ductile state at atmospheric pressure. In other words, the Tg corresponds to the temperature where the onset of segmental motion in the chains of the polymer occurs. Furthermore, the chemical structure of the polymer heavily influences the glass transition by affecting mobility.

The "melting temperature," $T_m$, of a polymer is the temperature at which an endothermal peak is observed in a DSC measurement, and where at least some of the crystallites begin to become disordered. The measured melting temperature may occur over a temperature range as the size of the crystallites, as well as presence of impurities and/or plasticizers, impacts the measured melting temperature of a polymer.

As used herein, a reference to the crystallinity of a polymer refers to the crystallinity as determined by standard DSC techniques.

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional or engineering stress, as applied to tension and compression tests, is force divided by the original gauge length.

"Strength" refers to the maximum stress along an axis which a material will withstand prior to fracture. The ultimate strength is calculated from the maximum load applied during the test divided by the original cross-sectional area.

"Radial strength" of a stent is defined as the pressure at which a stent experiences irrecoverable deformation. The loss of radial strength is followed by a gradual decline of mechanical integrity.

"Modulus" may be defined as the ratio of a component of stress or force per unit area applied to a material divided by the strain along an axis of applied force that results from the applied force. The modulus is the initial slope of a stress-strain curve, and therefore, determined by the linear hookean region of the curve. For example, a material has a tensile, a compressive, and a shear modulus.

"Strain" refers to the amount of elongation or compression that occurs in a material at a given stress or load, or in other words, the amount of deformation.

"Elongation" may be defined as the increase in length in a material which occurs when subjected to stress. It is typically expressed as a percentage of the original length.

"Toughness" is the amount of energy absorbed prior to fracture, or equivalently, the amount of work required to fracture a material. One measure of toughness is the area under a stress-strain curve from zero strain to the strain at fracture. The stress is proportional to the tensile force on the material and the strain is proportional to its length. The area under the curve then is proportional to the integral of the force over the distance the polymer stretches before breaking This integral is the work (energy) required to break the sample. The toughness is a measure of the energy a sample can absorb before it breaks. There is a difference between toughness and strength. A material that is strong, but not tough is said to be brittle. Brittle substances are strong, but cannot deform very much before breaking.

As used herein, a "drug" refers to a substance that, when administered in a therapeutically effective amount to a patient suffering from a disease or condition, has a therapeutic beneficial effect on the health and well-being of the patient. A therapeutic beneficial effect on the health and well-being of a patient includes, but it not limited to: (1) curing the disease or condition; (2) slowing the progress of the disease or condition; (3) causing the disease or condition to retrogress; or, (4) alleviating one or more symptoms of the disease or condition.

As used herein, a "drug" also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease or condition in the first place; (2) maintaining a disease or condition at a retrogressed level once such level has been achieved by a therapeutically effective amount of a substance, which may be the same as or different from the substance used in a prophylactically effective amount; or, (3) preventing or delaying recurrence of the disease or condition after a course of treatment with a therapeutically effective amount of a substance, which may be the same as or different from the substance used in a prophylactically effective amount, has concluded.

As used herein, "drug" also refers to pharmaceutically acceptable, pharmacologically active derivatives of those drugs specifically mentioned herein, including, but not limited to, salts, esters, amides, and the like.

EXAMPLES

The examples set forth below are for illustrative purposes only and are in no way meant to limit the invention. The following examples are given to aid in understanding the invention, but it is to be understood that the invention is not limited to the particular examples. The parameters and data are not to be construed to limit the scope of the embodiments of the invention.

Example 1

Free Radical Concentrations after E-beam Irradiation

The following example illustrates the effect on free radical concentration of exposing stent made from a polymer to a temperature above ambient temperature after sterilization with radiation. The stents used in the study are a scaffolding made from PLLA.

Figure 3:
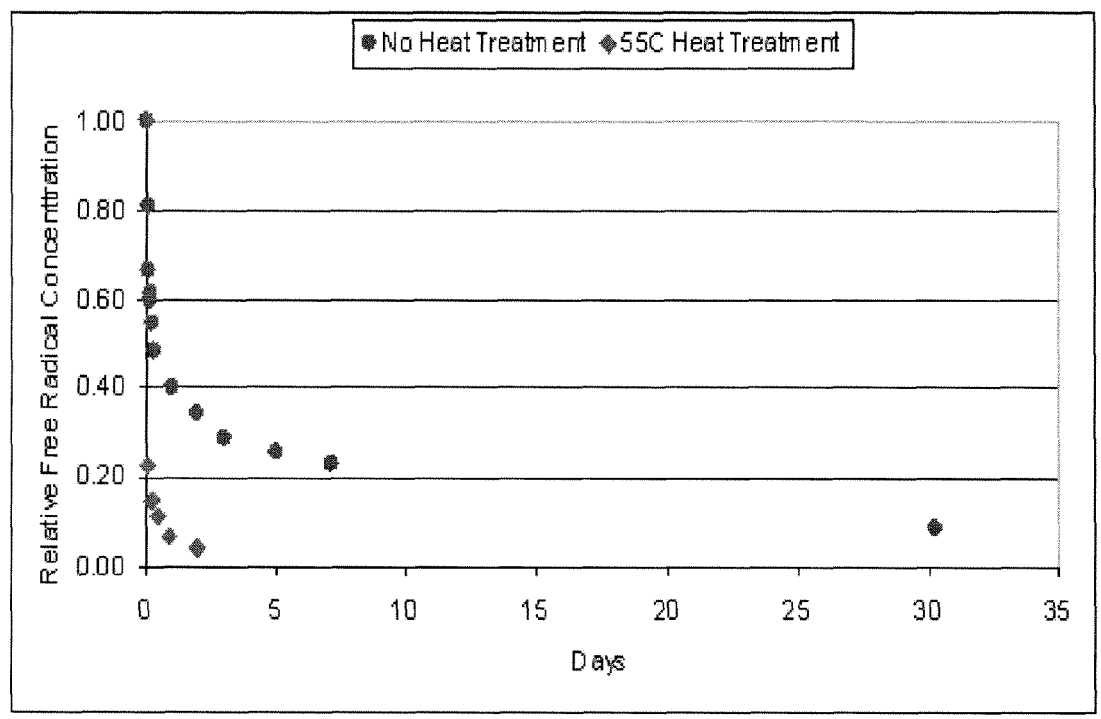
FIG. 3 depicts the relative free radical concentration of a polymeric stent with heat treatment and the stent with no heat treatment.

FIG. 3 and Table 2 depict the relative free radical concentration of the stent with heat treatment and the stent with no heat treatment as a function of time after e-beam sterilization. The relative free radical concentration is the free radical concentration normalized to the initial concentration immediately after e-beam sterilization. The stents in the study were sterilized by e-beam radiation with a dose of 31 kGy. The stents were packaged in a foil pouch (MARVELSEAL™ 360—Nylon/Aluminum/Low Density PolyEthylene (LDPE)) made by Oliver-Tolas of Grand Rapids, Mich. The packages were sealed with an argon atmosphere inside.

TABLE 2

Relative Free Radical Concentration of stents without and with heat treatment after e-beam sterilization.

| No Heat Treatment | | | 55° C. Heat Treatment | | |
| --- | --- | --- | --- | --- | --- |
| Days | Hours | Free Radical Concentration | Days | Hours | Free Radical Concentration |
| 0 | 0 | 1.00 | 0 | 0 | 1.00 |
| 0.04 | 1 | 0.81 | 0.08 | 2 | 0.23 |
| 0.08 | 2 | 0.66 | 0.21 | 5 | 0.15 |
| 0.13 | 3 | 0.61 | 0.42 | 10 | 0.11 |
| 0.17 | 4 | 0.60 | 0.92 | 22 | 0.07 |
| 0.25 | 6 | 0.54 | 2.00 | 48 | 0.04 |
| 0.33 | 8 | 0.48 | | | |
| 1.00 | 24 | 0.40 | | | |
| 2.00 | 48 | 0.35 | | | |
| 3.00 | 72 | 0.29 | | | |
| 5.00 | 120 | 0.26 | | | |
| 7.13 | 171 | 0.23 | | | |
| 30.21 | 725 | 0.09 | | | |

Each data point for both no heat treatment and heat treatment after e-beam exposure was generated by an individual packaged stent sample. The data for heat treatment was generated from stents subjected to a heat treatment in an oven for 2, 5, 10, 22, and 48 hours at 55° C. The free radical concentration for the stent samples not subjected to a heat treatment and the stent samples subjected to heat treatment was measured using Electron Spin Resonance (ESR), also known as Electron Paramagnetic Resonance (EPR), in Abbott Vascular, Temecula, Calif.

As shown by FIG. 3, the free radical concentration decays much faster with heat treatment than without. The free radical concentration is still at about 0.09 at 35 days with no heat treatment while the free radical concentration is less than half of that, 0.04, after only about 2 days.

Figure 4:
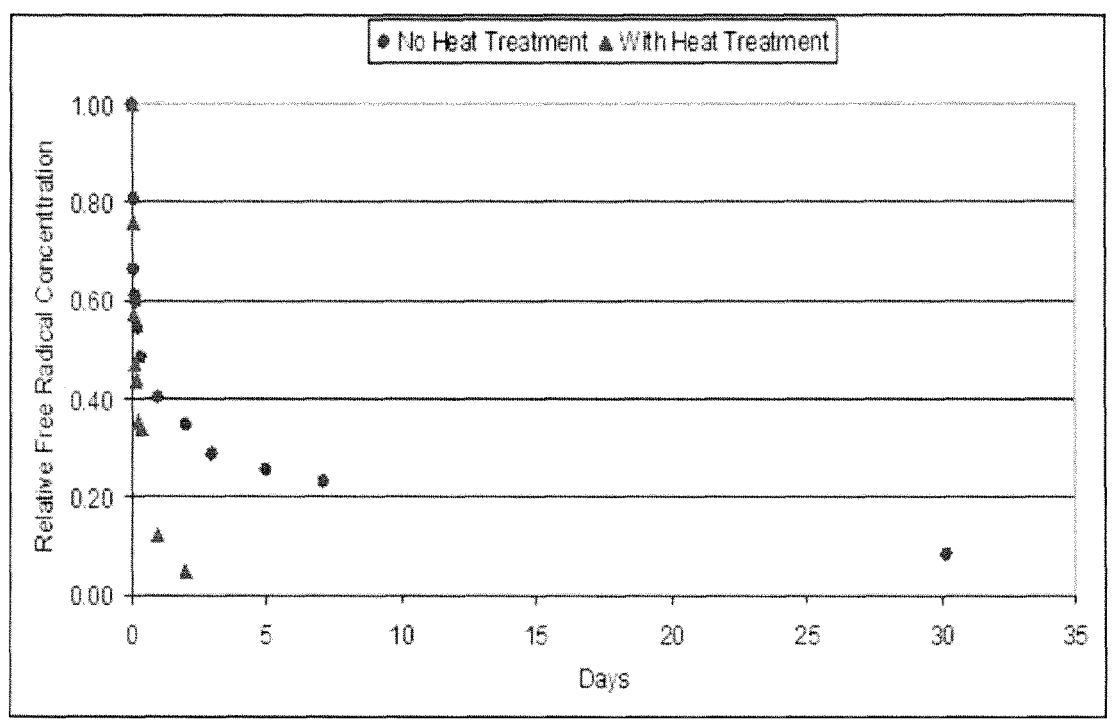
FIG. 4 depicts the relative free radical concentration of a polymeric stent with heat treatment and the stent with no heat treatment.

FIG. 4 also depicts the relative free radical concentration of the stent with heat treatment and the stent with no heat treatment. The data for the no heat treatment is the same as that in FIG. 5. One data point in FIG. 4 for heat treatment was generated from a stent subjected to a heat treatment in a oven for 5 hours at 55° C., which is from FIG. 3. The additional data points for the curve with heat treatment are predicted by pseudo first order decay kinetics with free radical concentration of sample after 5 hours at 55° C. heat treatment. A comparison of FIG. 3 and FIG. 4 shows that the kinetic model predicts a greater relative free radial concentration with time than the experimental data. Therefore, the model may be used to select a desirable heat treatment temperature. For example, the relative free radical concentration can be measured for various temperatures and the decay profile may then be calculated from the single data points. The decay profiles may be expected to provide an upper bound to the decay of the free radical concentration vs. time for the various temperatures.

Example 2

Number-Average Molecular Weight after E-beam Irradiation

Polymeric stents manufactured from poly(L-lactide) (PLLA). Polymer tubes were extruded from Poly(L-lactide) (PLLA), RESOMER® L 210 S, supplied by Boehringer Ingelheim by extrusion of a polymer tube, biaxially expanding the polymer tube such that the radial expansion was within about 400% to about 500% and the axial expansion was within about 20% to about 120%, and laser cutting a stent pattern into the tube to form the stent. Subsequently, radiopaque markers were placed in the stent, and then a drug delivery coating including a polymer and a drug (PDLLA and everolimus) was applied. The stent was crimped onto a balloon catheter at a temperature of about 40° C. to about 55° C. The stents were packaged in a foil pouch (MARVELSEAL™ 360—Nylon/Aluminum/LDPE) made by Oliver-Tolas of Grand Rapids, Mich. The packages were sealed with an argon atmosphere inside. The stents in the study were sterilized by e-beam radiation with a dose of 31 kGy.

The number-average molecular weight was determined as a function of time after sterilization. The number-average molecular weight prior to sterilization was about 180 to about 200 KDaltons. Immediately following sterilization, the number-average molecular weight was measured to be about 78 KDaltons. As shown in FIG. 5, the number-average molecular weight increased with the time after sterilization reaching a plateau of about 115 KDaltons after about 21 days when stored at room temperature (25° C.±3° C.).

Example 3

Radial Strength after E-beam Irradiation

Polymeric stents were manufactured from poly(L-lactide) (PLLA), coated, crimped, and sterilized as described in Example 2. The radial strength was determined by as the pressure at which irrecoverable deformation was observed. The testing utilized a MSI RX550™ Radial Force Tester equipment at a rate of 0.5 mm/second, and testing was conducted at 37° C. The radial strength of the polymeric stents were measured as a function of time after sterilization. The stents were maintained at room temperature (25° C.±3° C.) from the time of sterilization to measurement. As shown in FIG. 6, the radial strength decreases as a function of time after sterilization, reaching a "pseudo-steady state," "pseudo-equilibrium," or plateau value at about 60 days.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true sprit and scope of this invention. Moreover, although individual aspects or features may have been presented with respect to one embodiment, a recitation of an aspect for one embodiment, or the recitation of an aspect in general, is intended to disclose its use in all embodiments in which that aspect or feature can be incorporated without undue experimentation. Also, embodiments of the present invention specifically encompass embodiments resulting from treating any dependent claim which follows as alternatively written in a multiple dependent form from all prior claims which possess all antecedents referenced in such dependent claim (e.g. each claim depending directly from claim 1 should be alternatively taken as depending from any previous claims).

What is claimed is:

1. A method for conditioning a polymeric stent, the method comprising:
    exposing a polymeric stent with a polymeric scaffolding consisting essentially of poly(L-lactide) to a temperature of 30° C. to 35° C. or 35° C. to 40° C. for a duration of time, the duration of time being 1 day to 20 days;
    wherein the polymeric stent has been crimped onto a delivery device, packaged, and sterilized prior to the exposure;
    wherein the polymeric scaffolding is formed from a polymeric tube consisting essentially of poly(L-lactide) that has been deformed by application of stress, the deformation comprising radial expansion of the polymeric tube at a temperature greater than that of the glass transition temperature of the polymeric tube.

2. The method of claim 1, wherein the exposure temperature is from about 32° C. to about 40° C.

3. The method of claim 2, wherein the duration of exposure is from about 1 day to about 10 days.

4. A method for conditioning a polymeric stent, the method comprising:
    exposing a polymeric stent with a polymeric scaffolding consisting essentially of poly(L-lactide) to a temperature equal to, approximately equal to, or greater than 30° C. and not more than about 55° C. for a duration of time, the duration of time being at least 8 hours;
    wherein the polymeric stent has been crimped onto a delivery device, packaged, and sterilized prior to the exposure;
    wherein the polymeric scaffolding is formed from a polymeric tube consisting essentially of poly(L-lactide) that has been deformed by application of stress, the deformation comprising radial expansion of the polymeric tube at a temperature greater than that of the glass transition temperature of the polymeric tube; and
    exposing the polymeric stent with the polymeric scaffolding to a temperature equal to or greater than 35° C. and not more than about 70° C. for a duration of time, the duration of time being from about 4 hours to about 6 days, after the polymeric stent has been crimped onto a delivery device, but before the polymeric stent has been sterilized.

5. The method of claim 4, wherein the duration of the exposure after crimping and before sterilizing is from about 16 hours to about 48 hours, and the temperature of the exposure after crimping and before sterilization is from about 45° C. to about 65° C.

6. The method of claim 5, wherein the duration of the exposure after crimping and before sterilizing is from about 16 hours to about 32 hours, and the temperature of the exposure after crimping and before sterilization is from about 50° C. to about 65° C.

7. The method of claim 1, wherein the polymeric stent is crimped onto a delivery device at a temperature in the range of about 45° C. to about 50° C.

8. The method of claim 7, wherein the post-sterilization exposure temperature is in the range from about 33° C. and not more than about 37° C., and the duration of the post-sterilization exposure is in the range of about 32 hours to about 84 hours.

9. The method of claim 8, wherein the polymeric stent is crimped onto a delivery device at a temperature of about 48° C., and wherein the post-sterilization exposure temperature is about 35° C., and the duration of the post-sterilization exposure is in the range of about 48 hours to about 72 hours.

10. The method of claim 1, wherein the duration of time is 3 days to 20 days.

* * * * *